US00PP10918P

United States Patent [19]

Pouw

[11] Patent Number: Plant 10,918

[45] Date of Patent: May 25, 1999

[54] HYBRID TEA ROSE PLANT NAMED 'RUILAV'

[75] Inventor: A. A. Pouw, De Kwakel, Netherlands

[73] Assignee: De Ruiter's Nieuwe Rozen B.V., De Kwakel, Netherlands

[21] Appl. No.: 08/921,123

[22] Filed: Aug. 28, 1997

[51] Int. Cl.[6] ..... A01H 5/00

[52] U.S. Cl. ..... Plt./137

[58] Field of Search ..... Plt./11, 18, 19, Plt./130, 137, 138

[56] References Cited

U.S. PATENT DOCUMENTS

P.P. 3,543 5/1974 Meilland ..... Plt./18

P.P. 4,940 11/1982 Olesen et al. ..... Plt./11

P.P. 9,185 7/1995 van der Meer ..... Plt./18

P.P. 9,807 2/1997 van der Meer ..... Plt./18

OTHER PUBLICATIONS

UPOU–ROM, Jan. 1998, Plant Variety Database, GTI Jouve Retrieval Software, Citation for 'Panrav', and 'Ruilav'.

*Primary Examiner*—Howard J. Locker

*Attorney, Agent, or Firm*—Christie, Parker & Hale, LLP

[57] ABSTRACT

A new variety of hybrid tea rose plant producing deep pink flowers of good form and suitable for growing under glass.

1 Drawing Sheet

BACKGROUND OF THE INVENTION

The present invention relates to a new and distinct variety of rose plant of the hybrid tea rose class which was created by crossing undistributed, unnamed and unpatented seedlings as seed and pollen parents in De Kwakel, Holland. The varietal denomination of the new variety is 'Ruilav'. The new variety was isolated and asexually reproduced by budding in The Netherlands.

SUMMARY OF THE INVENTION

Among the novel characteristics possessed by this new variety which distinguish it from its parents and all other varieties of which I am aware are its attractive deep pink flowers of good form borne on a floriferous plant with long stems and suitable for production of cut flowers under glass. The new variety has been reproduced through propagation by cuttings, grafting, budding and micropropagation.

Asexual reproduction by budding of the new variety as performed in De Kwakel, Holland, shows that the foregoing and other distinguishing characteristics come true to form and are established and transmitted through succeeding propagations.

BRIEF DESCRIPTION OF ILLUSTRATION

The accompanying illustration shows a typical specimen of the vegetative growth and flower of the new variety depicted in color as nearly true as it is reasonably possible to make the same in a color illustration of this character.

DESCRIPTION OF THE NEW VARIETY

The following is a detailed description of the new variety, with color terminology in accordance with The Royal Horticultural Society Colour Chart (R.H.S.C.C.) and horticultural terminology in accordance with standard terminology used in UPOV-approved horticultural guidelines. The terminology used in color descriptions herein refers to plate numbers in the aforementioned color chart. Phenotypic expression may vary deepening upon growing conditions under different climate, soil, and cultivation conditions.

Parentage: Seed and pollen parents are unnamed seedlings.
Class: Hybrid Tea.

The following further horticultural description is based on observations made of specimens grown under glass in De Kwakel, Holland.

Flower

Blooming habit: Nearly continuous, under glass in The Netherlands about 280 stems/m$^2$/year.

A. Bud:

(1) *Size.*—Medium, about 1 to 1.5 inches long and about 1 inch wide after sepals separate and spread.

(2) *Form.*—Ovate (shape of longitudinal section just before separation of sepals); urn-shaped after sepals part.

(3) *Color.*—As sepals divide, near 51A to 51B with occasional white streak.

(4) *Sepals.*—Above green bud, about same length as bud showing color; top near 146C with light center line and some have purplish tip and margin; underside darker green; reflex back; some foliaceous.

(5) *Peduncle.*—About 3¾ inches in length; strength-erect; strong; color-medium green, near 146A to 146B, few hairs on peduncle.

B. Flower: Medium; viewed from above — star-shaped; viewed from side — (a) upper part of fully opened flower, flattened convex; (b) lower part of fully opened flower, flat.

(1) *Size.*—Average size when fully expanded — about 4 to 5 inches.

(2) *Borne.*—Singly, one to a stem.

(3) *Form.*—Pointed center, spiral imbricated, some outer petals ruffled, most outer petals reflex to points.

(4) *Petalage.*—Fully double, about 25 to 30.

(5) *Color.*—Color of petal top surface in ⅓ to full open bloom appears near 62C with red tips, near 57B; outermost petals have brownish purple tones, near 182C and 199C; petal undersurface near 185C to 185D; inner petals undersurface have somewhat lighter coloration. Color of petal at point of attachment near 2C. Oveall tonality from a distance is attractive deep pink.

(6) *Peduncle.*—Smooth.

(7) *Fragrance.*—Absent or very weak.

(8) *Length of stems.*—About 20 to 30 inches.

Petals:

(1) *Texture.*—Crisp.

(2) *Appearance.*—Top slightly velvety and underside more matte.

(3) *Form and size.*—Broad, medium, strong undulation of margin.

(4) *Arrangement.*—Regularly arranged, imbricated.

(5) *Petaloids.*—About 35, crinkled, about same color as petals.

(6) *Lasting quality.*—On plant about 3 or more weeks, about 15 days after cutting.

Reproductive Organs

A. Stamens, filaments and anthers:

*Arrangement and color.*—Regularly arranged around styles; color of filaments — white.

B. Pollen:

*Color.*—Red.

C. Styles: Long, stigma above mouth of receptacle, light yellow.

D. Stigmas: Yellow, positioned below anthers.

E. Hip: Pitcher-shaped; very small to small seed vessel at petal fall.

Plant

A. Form: Narrow, bushy, average disease resistance, height about 1.2 m, spread about 0.4 m.

B. Growth: Vigorous.

C. Foliage: Compound 3 and 5 leaflets, sometimes 7 leaflets.

(1) *Size.*—Medium width and length.

(2) *Quantity.*—Abundant.

(3) *Color.*—Juvenile foliage — upper side near 185A to 185B, under side near 185B; weak anthocyanin coloration, (shoot about 20 cm long); mature leaf color — upper side near 136A, under side near 137B to 137C.

(4) *Shape.*—Broad oval.

(5) *Texture.*—Upper side is glossy; underside is matte.

(6) *Edge.*—Serrated.

(7) *Serration.*—Serrate to doubly serrate, acuminate to cuspidate apices.

(8) *Leaf stem.*—Color — near 147A to 147B.

(9) *Stipules.*—Short, simple, medium green, distinct auricle.

(10) *Leaflets.*—Cross section — flat: medium undulation of margin; terminal leaflet — medium length and medium width; blade about 3 to 4 inches long and 2 to 3 inches wide, obtuse base.

D. Wood:

(1) *New wood.*—Color — young shoots have weak to medium anthocyanin; coloration — bronze red purple.

(2) *Old wood.*—Color — near 185A to 185B.

E. Prickles (thorns):

(1) *Prickles.*—Present; quantity (main stalk) — ordinary; shape of lower side — flat; Quantity — short prickles absent or very few, long prickles medium; Color — near 176C to 176B; Position — irregular.

What is claimed is:

1. A new and distinct rose plant of the variety substantially as shown and described.

* * * * *

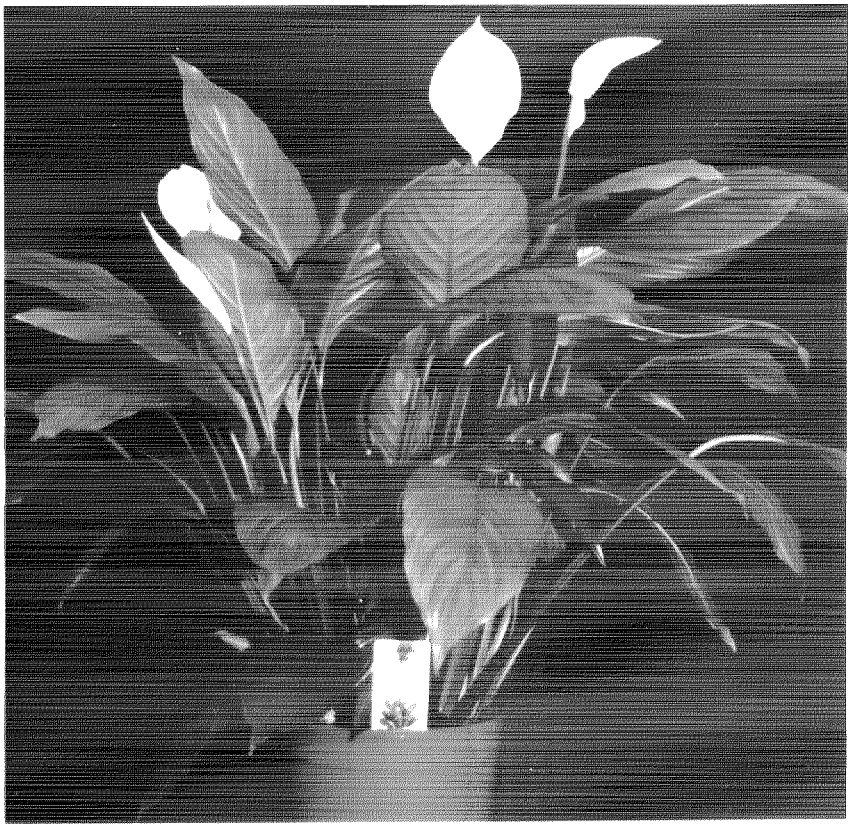
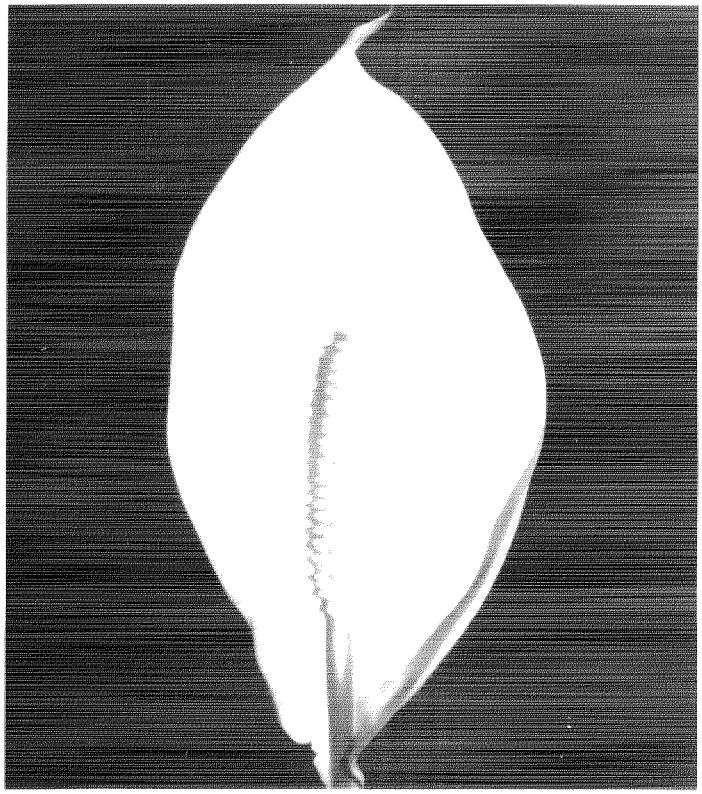

UNITED STATES PATENT AND TRADEMARK OFFICE

CERTIFICATE OF CORRECTION

PATENT NO. : PP 10,918
APPLICATION NO. : 08/921123
DATED : May 25, 1999
INVENTOR(S) : A. A. Pouw It is certified that error appears in the above-identified patent and that said Letters Patent is hereby corrected as shown below:

DELETE Drawing Sheet SUBSTITUTE therefor the Drawing Sheet shown on the attached page.

Signed and Sealed this

Third Day of February, 2009

John Doll

JOHN DOLL
*Acting Director of the United States Patent and Trademark Office*

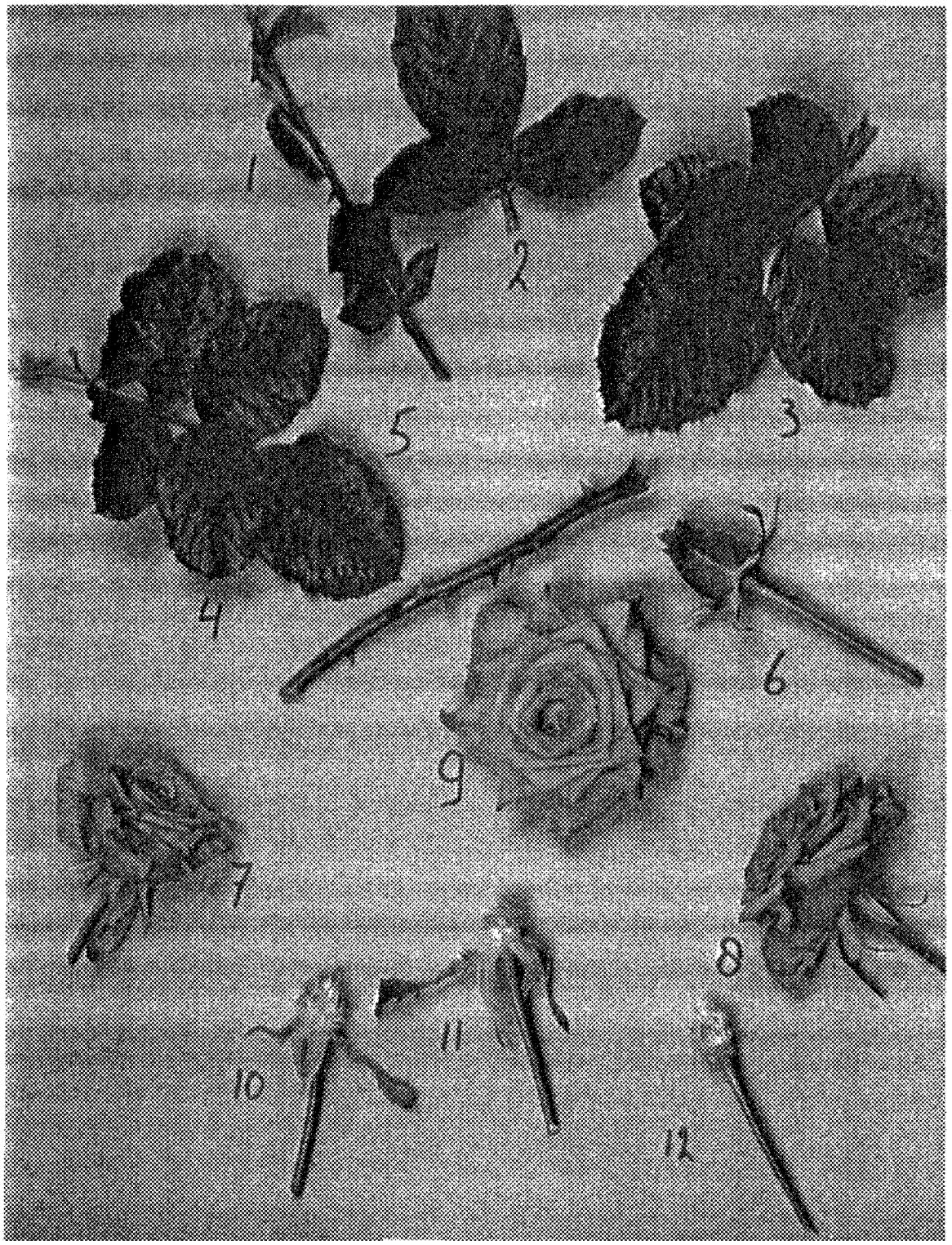
1
2
3
4
5
6
7
8
9
10
11
12

UNITED STATES PATENT AND TRADEMARK OFFICE

CERTIFICATE OF CORRECTION

PATENT NO. : PP 10,918
APPLICATION NO. : 08/921123
DATED : May 25, 1999
INVENTOR(S) : A. A. Pouw It is certified that error appears in the above-identified patent and that said Letters Patent is hereby corrected as shown below:

DELETE Drawing Sheet SUBSTITUTE therefor the Drawing Sheet shown on the attached page.

This certificate supersedes the Certificate of Correction issued February 3, 2009.

Signed and Sealed this

Seventh Day of April, 2009

JOHN DOLL
*Acting Director of the United States Patent and Trademark Office*

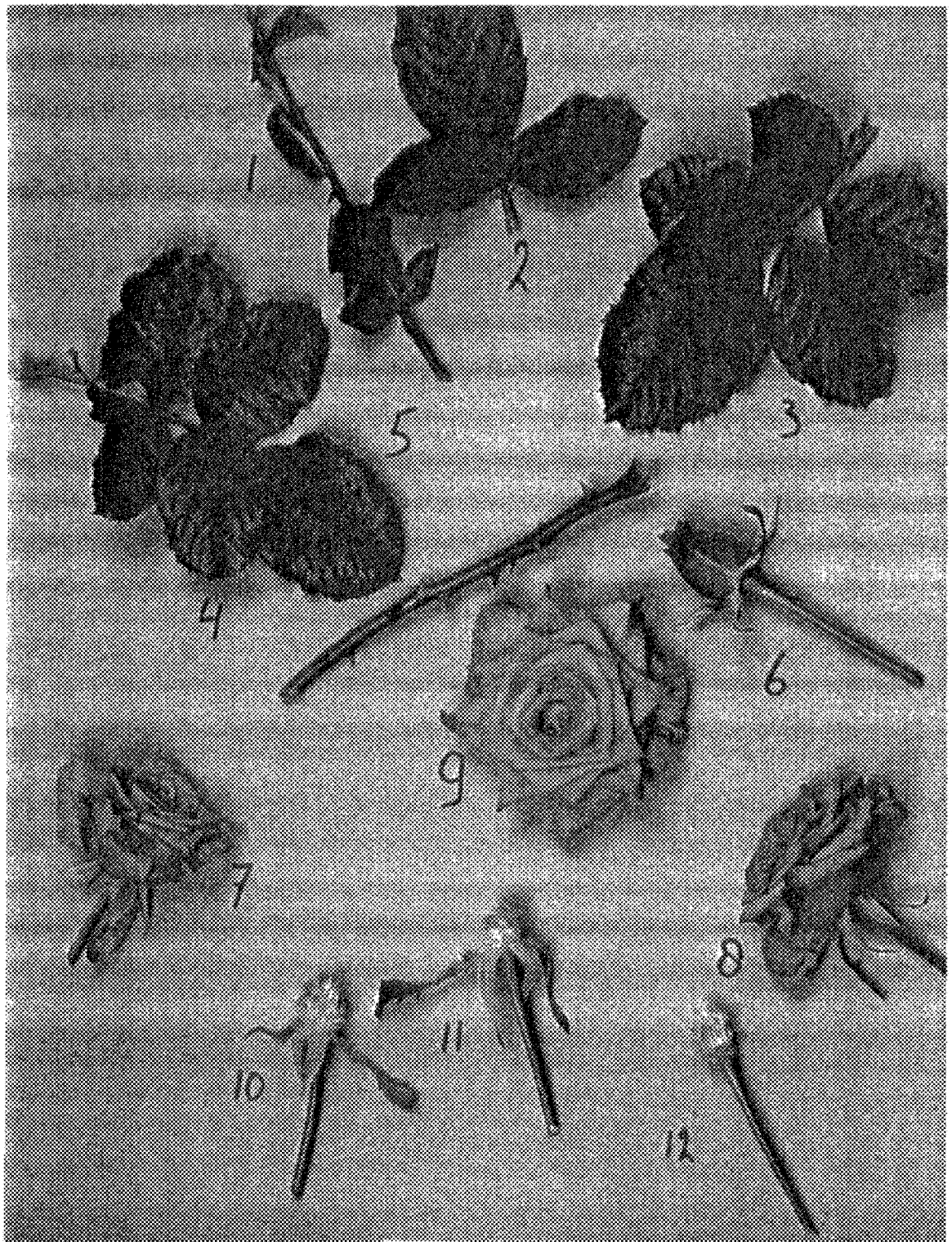
1
2
3
4
5
6
7
8
9
10
11
12